US011555874B2

(12) United States Patent
Dupuis et al.

(10) Patent No.: US 11,555,874 B2
(45) Date of Patent: Jan. 17, 2023

(54) SYSTEM AND METHOD FOR REAL-TIME MAGNETIC RESONANCE IMAGING DATA VISUALIZATION IN THREE OR FOUR DIMENSIONS

(71) Applicant: Case Western Reserve University, Cleveland, OH (US)

(72) Inventors: Andrew Dupuis, Cleveland, OH (US); Nicole Seiberlich, Shaker Heights, OH (US); Dominique Franson, Cleveland, OH (US); Mark A. Griswold, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/681,454

(22) Filed: Nov. 12, 2019

(65) Prior Publication Data
US 2020/0150197 A1 May 14, 2020

Related U.S. Application Data

(60) Provisional application No. 62/758,818, filed on Nov. 12, 2018.

(51) Int. Cl.
| | |
|---|---|
| *G01R 33/28* | (2006.01) |
| *G01R 33/56* | (2006.01) |
| *G06T 11/00* | (2006.01) |
| *G06F 3/04815* | (2022.01) |
| *G06F 3/04845* | (2022.01) |
| *A61B 34/20* | (2016.01) |
| *A61B 5/00* | (2006.01) |

(Continued)

(52) U.S. Cl.
CPC ............ *G01R 33/286* (2013.01); *A61B 5/055* (2013.01); *A61B 5/7285* (2013.01); *A61B 34/20* (2016.02); *G01R 33/5608* (2013.01); *G06F 3/017* (2013.01); *G06F 3/04815* (2013.01); *G06F 3/04845* (2013.01); *G06T 11/003* (2013.01); *A61B 2034/2051* (2016.02); *A61B 2034/2065* (2016.02); *G06T 2210/41* (2013.01)

(58) Field of Classification Search
CPC ................ G01R 33/286; G01R 33/546; G01R 33/5608; G06F 3/017; G06F 3/04815; G06F 3/04845; G06T 11/003; G06T 2210/41
USPC ................................................. 345/156–169
See application file for complete search history.

(56) References Cited

U.S. PATENT DOCUMENTS

| | | | |
|---|---|---|---|
| 10,194,131 B2 * | 1/2019 | Casas ...................... G06F 3/011 |
| 2013/0338930 A1 * | 12/2013 | Senegas ............... G01R 33/546 |
| | | | 702/19 |

(Continued)

*Primary Examiner* — Kwin Xie
(74) *Attorney, Agent, or Firm* — Quarles & Brady LLP

(57) ABSTRACT

A system for displaying and interacting with magnetic resonance imaging (MRI) data acquired using an MRI system includes an image reconstruction module configured to receive the MRI data and to reconstruct a plurality of images using the MRI data, an image rendering module coupled to the image reconstruction module and configured to generate at least one multidimensional image based on the plurality of images and a user interface device coupled to the image rendering module and located proximate to a workstation of the MRI system. The user interface device is configured to display the at least one multidimensional image in real-time and to facilitate interaction by a user with the multidimensional image in a virtual reality or augmented reality environment.

20 Claims, 4 Drawing Sheets

(51) Int. Cl.
*A61B 5/055* (2006.01)
*G06F 3/01* (2006.01)

(56) References Cited

U.S. PATENT DOCUMENTS

| | | | |
|---|---|---|---|
| 2016/0026253 A1* | 1/2016 | Bradski | H04N 13/128 345/8 |
| 2017/0258526 A1* | 9/2017 | Lang | A61B 17/1764 |
| 2019/0278436 A1* | 9/2019 | Gulaka | G06F 3/0482 |
| 2020/0107904 A1* | 4/2020 | Silva | G06F 3/017 |

* cited by examiner

SYSTEM AND METHOD FOR REAL-TIME MAGNETIC RESONANCE IMAGING DATA VISUALIZATION IN THREE OR FOUR DIMENSIONS

CROSS-REFERENCE TO RELATED APPLICATION

This application is based on, claims priority to, and incorporates herein by reference in its entirety U.S. Ser. No. 62/758,818 filed Nov. 12, 2018 and entitled "System and Method For Real-Time Magnetic Resonance Imaging Data Visualization In Three or Four Dimensions."

STATEMENT REGARDING FEDERALLY SPONSORED RESEARCH OR DEVELOPMENT

This invention was made with government support under the grant(s) HL094557 and EB018108 awarded by the National Institutes of Health, and grant 1563805 awarded by the National Science Foundation. The government has certain rights in the invention.

FIELD

The present disclosure relates generally to magnetic resonance imaging (MRI) systems and, more particularly, to a system and method for visualizing and interacting with MRI data in three and four dimensions in real-time.

BACKGROUND

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel on another. If, however, the substance, or tissue, is subjected to a magnetic field (excitation field $B_1$, also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

Magnetic resonance imaging (MRI) systems may be employed to provide guidance to interventionalists who are performing interventional procedures that diagnose or treat tissue within a patient. In interventional procedures, an interventional device may be guided by an interventionalist to a target tissue within a patient. Interventional devices may include, for example, needles, catheters, ablation devices, imaging devices, therapeutic devices, diagnostic devices, and so on. An MRI system may be used to generate images in real-time or near real-time that are used to assist the interventionalist in guiding an interventional device. For example, in an image-guided intervention such as device insertion the MRI system may be used to determine the location of the interventional device relative to the surrounding anatomy and the target tissue.

SUMMARY OF THE DISCLOSURE

In accordance with an embodiment, a system for displaying and interacting with magnetic resonance imaging (MRI) data acquired using an MRI system includes an image reconstruction module configured to receive the MRI data and to reconstruct a plurality of images using the MRI data, an image rendering module coupled to the image reconstruction module and configured to generate at least one multidimensional image based on the plurality of images and a user interface device coupled to the image rendering module and located proximate to a workstation of the MRI system. The user interface device is configured to display the at least one multidimensional image in real-time and to facilitate interaction by a user with the multidimensional image in a virtual reality or augmented reality environment.

In accordance with another embodiment, a method for displaying and interacting with magnetic resonance imaging (MRI) data acquired using an MRI system includes receiving the MRI data from the MRI system, reconstructing a plurality of images using the MRI data with an image reconstruction module, generating at least one multidimensional image based on the plurality of images using an image rendering module, displaying the at least one multidimensional image in real-time on a user interface device located proximate to a workstation of the MRI system and interacting with the multidimensional image in a virtual reality or augmented reality environment using the user interface device.

BRIEF DESCRIPTION OF THE DRAWINGS

The present invention will hereafter be described with reference to the accompanying drawings, wherein like reference numerals denote like elements.

DETAILED DESCRIPTION

Figure 1:
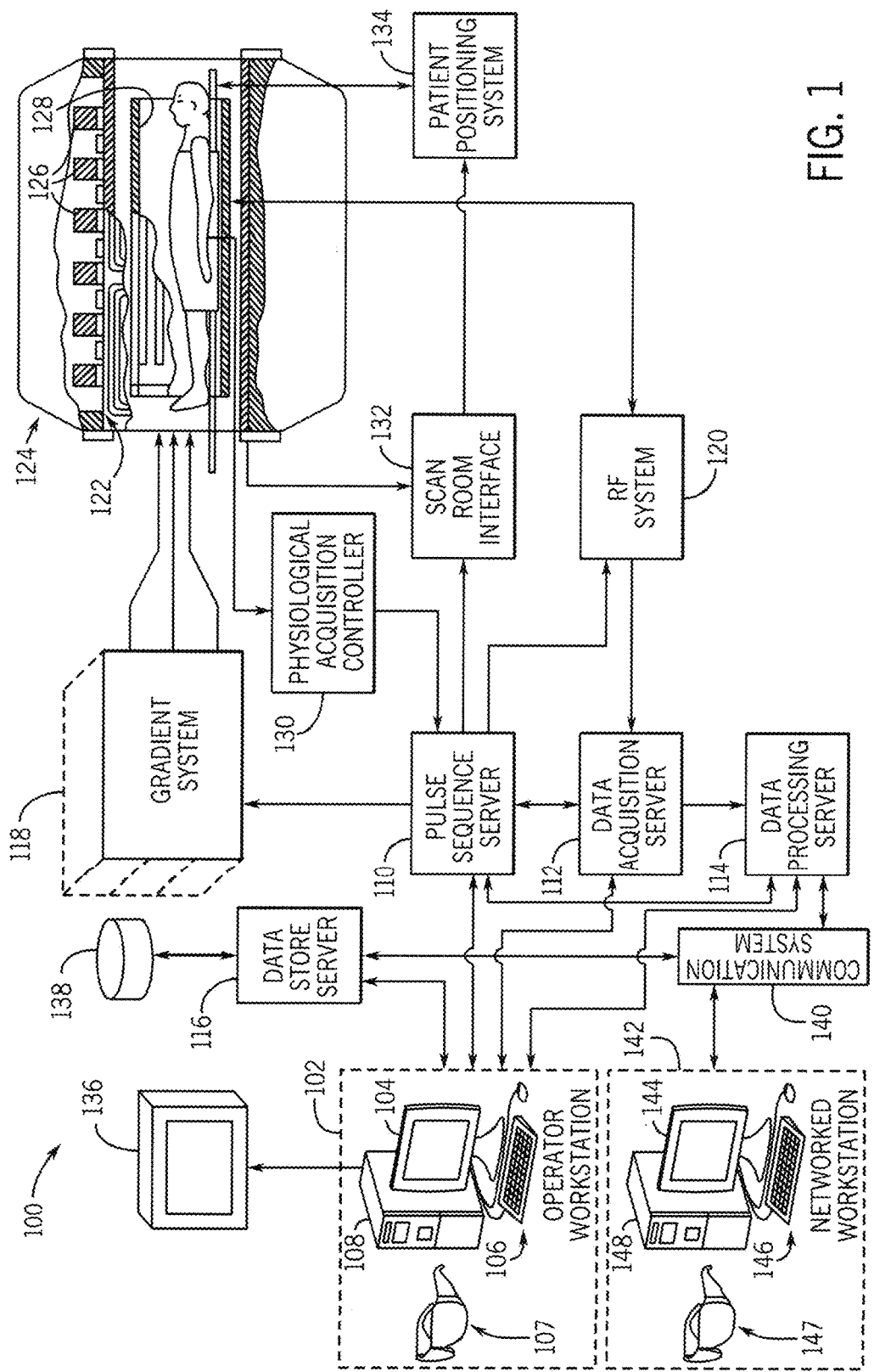
FIG. 1 is a schematic diagram of an MRI system in accordance with an embodiment.

FIG. 1 shows an MRI system 100 in accordance with an embodiment. MRI system 100 may be used to implement the methods described herein. MRI system 100 includes an operator workstation 102, which may include a display 104, one or more input devices 106 (e.g., a keyboard, a mouse), and a processor 108. Though the display 104 is illustrated as a monitor and the input device 106 is illustrated as including a mouse and keyboard in FIG. 1, these components can be supplemented with or replaced by hardware and software that facilitates virtual reality (VR), augmented reality (AR), or the like. For example, a VR (or AR) headset 107 may be provided. This VR headset 107 is a non-limiting example of just one virtual reality component and may be replaced or supplemented with other hardware for virtual reality or augmented reality. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (1)$$

and the phase of the received magnetic resonance signal may also be determined according to the following relationship:

$$\varphi = \tan^{-1}\left(\frac{Q}{I}\right). \qquad (2)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processing server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136 or a VR (or AR) headset 107. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse or VR or AR headset 147), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

In an embodiment, MRI system 100 may be used during an interventional procedure (e.g., ablation, biopsy, implanting of a medical device, etc.) to assist an operator in guiding an interventional device within a patient. Interventional devices include, for example, needles, catheters, ablation devices, imaging devices, therapeutic devices, diagnostic devices, etc. During an interventional procedure, the MRI system is used to generate images that may be used by the operator to determine and monitor the location of the interventional device. In an embodiment, the MRI system 100 may be configured to employ passive and/or active tracking techniques to track the interventional device. Passive tracking techniques may include, for example, paramagnetic markers and intravascular contrast agents that may be used to visualize the interventional device. Active tracking techniques include, for example, mounting a radiofrequency (RF) receiver coil (or tracking coil) on the interventional device or using a guide wire as a linear receive coil. The MRI system may then be used to track the position of the interventional device based on the position of the tracking coil. While MRI system 100 as shown in FIG. 1 illustrates a closed MRI system, in an embodiment, the MRI system 100 may be an open MRI system that is designed to allow an operator access to a region of interest in the patient such as during an interventional procedure.

The present disclosure describes a system and method for visualizing and interacting with MRI data in three and four dimensions in real-time. As mentioned above, the display 104 and the input device 106 of the operator workstation 102 of the MRI system 100 may be supplemented with or replaced by hardware and software that facilitates virtual reality (VR), augmented reality (AR), or the like. In various embodiments, the MRI system 100 including the VR (or AR) components (e.g., a VR headset 107) is configured to allow an operator to view multidimensional renderings of multiple slices of MRI images and interact with the multi-dimensional rendering. In an embodiment, the visualization of and interaction with the multidimensional rendering is in real-time, e.g., during an interventional procedure. In another embodiment, an operator may use the system to retrospectively view multidimensional renderings. The system and method described herein provide features to an operator (e.g., at the operator workstation 102) of the MRI system 100 that are typically only available in a standard radiology reading room. The system and method for real-time visualization of magnetic resonance imaging data will be discussed in further detail with respect to FIG. 2 below.

Figure 2:
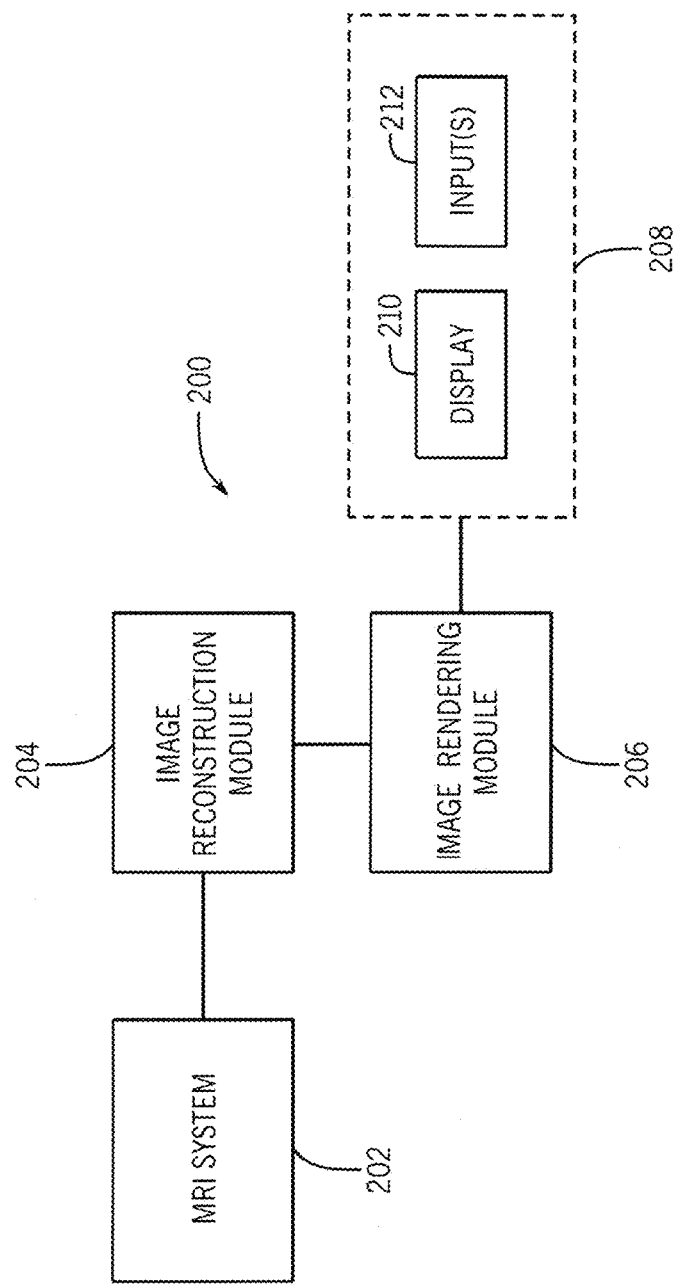
FIG. 2 is a block diagram of a system for real-time magnetic resonance imaging data visualization in three or four dimensions in accordance with an embodiment.

FIG. 2 is a block diagram of a system for real-time magnetic resonance imaging data visualization in three or four dimensions in accordance with an embodiment. System 200 includes an MRI system 202, an image reconstruction module 204, an image rendering module 206 and a user interface device 208. MRI system 202 may be, for example, the MRI system 100 illustrated in FIG. 1. As described above with respect to FIG. 1, the MRI system 202 may be used to acquire MRI data using known data acquisition techniques. The acquired MRI data may be two-dimensional or three dimensional. Image reconstruction module 204 is coupled to the MRI system 202 and is configured to receive the MRI data acquired by the MRI system 202 and reconstruct a plurality of images (or image slices) using known reconstruction methods. For example during an interventional procedure under MRI guidance an operator may acquire MRI data and reconstruct images at multiple intersecting slice locations in order to gain a 3D perspective of a region of interest. The reconstructed images may be two dimensional or three dimensional images. In an embodiment, the MRI system 202 and image reconstruction modules 204 are configured to implement parallel imaging techniques to acquire MRI data and reconstruct images. Parallel imaging makes it possible to collect accelerated MRI data and reconstruct images at high frame rates. In some parallel imaging implementations, a calibration step must be performed at each desired slice at the beginning of an imaging session. In an embodiment, image reconstruction module 204 may be implemented as part of the MRI system 202, for example, data processing server 114 shown in FIG. 1. In another embodiment, image reconstruction module 204 may be implemented on a separate computer system (e.g., the computer system described below with respect to FIG. 4) that is coupled to the MRI system 202.

Figure 3:
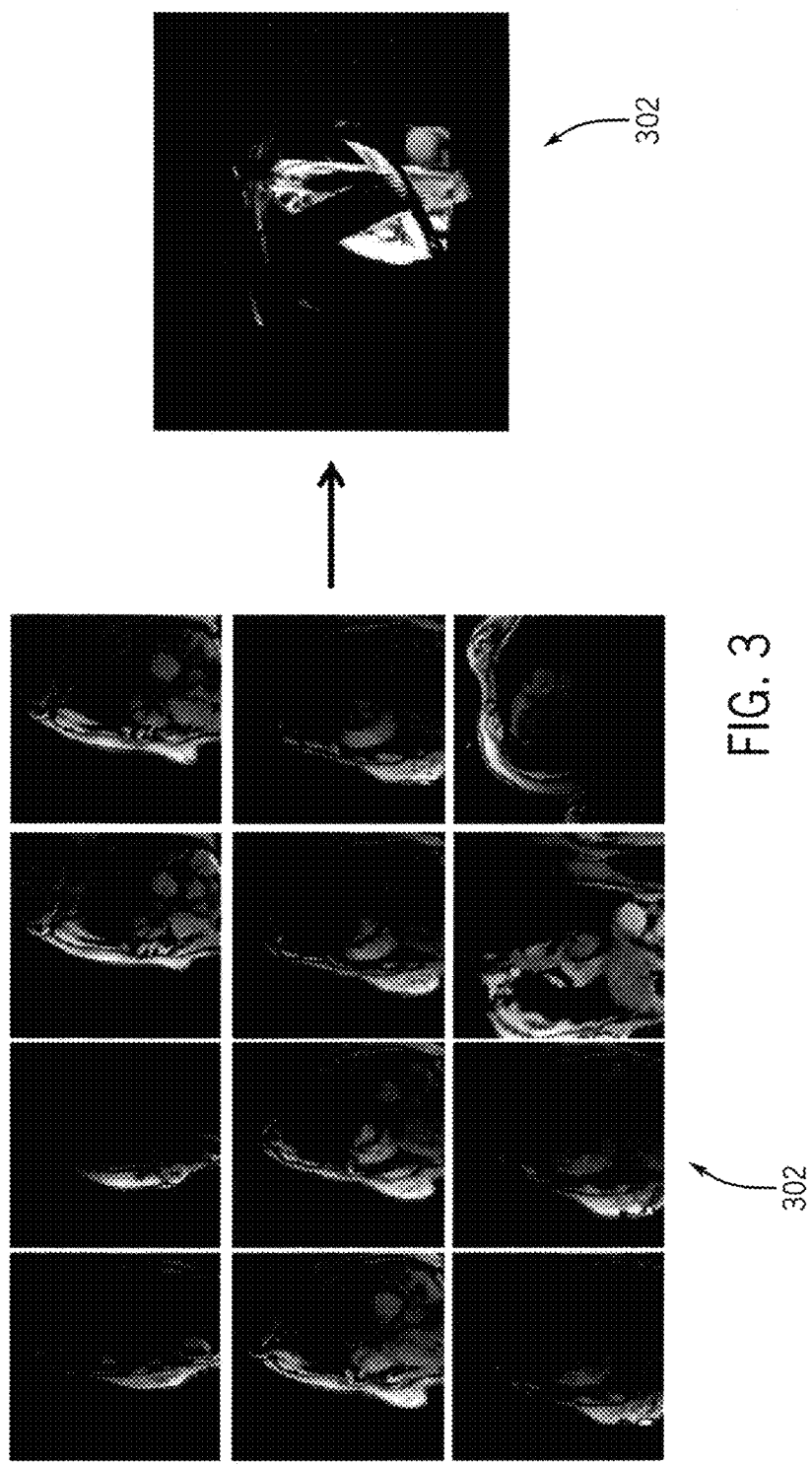
FIG. 3 shows an example rendering from image slices of the heart in accordance with an embodiment.

An image rendering module 206 is coupled to the image reconstruction module 204 and is configured to receive the plurality of reconstructed images (or image slices) and to generate a three dimensional or four dimensional rendering (e.g., a hologram) of the images as a spatialized object using, for example, known rendering techniques. The slices may be rendered in their acquired positions and orientations within a common coordinate frame, creating a three dimensional or four dimensional representation of the region being imaging. The multidimensional rendering may be used to present the plurality of slices in an organized and intuitive manner as described further below. As mentioned above, the MRI data may be acquired and images reconstructed using parallel imaging techniques. If parallel imaging is used, an initial, accelerated image may be collected at each pre-calibrated slice location to initialize the image rendering system 206 with the total number of number of available slices, the image matrix size and the slice positions and orientations. Thereafter, arbitrary subsets of these slices may be collected without re-initializing the rendering system until the slice positions or orientations change. The MRI slice data may be acquired by the MRI system 202, reconstructed by the image reconstruction module 204 and sent to the rendering system on a sequential slice-by-slice basis. In one embodiment, the rendering may be updated only when all of the slices in a frame are available. Alternatively, the rendering may be updated each time a slice is reconstructed. In an embodiment, image rendering module 206 may implemented as part of the MRI system 202, for example, on processor 108 of the operator workstation 102 shown in FIG. 1. In another embodiment, image rendering module 206 may be implemented on a separate computer system (e.g., the computer system described below with respect to FIG. 4) that is coupled to the image reconstruction module 204. FIG. 3 shows an example rendering from image slices of the heart in accordance with an embodiment. In FIG. 3 multiple slices 302 showing common views of the heart are rendered into a multidimensional rendering 304 using, for example, known techniques.

Returning again to FIG. 2, a user interface device 208 is coupled to the image rendering module 206 and includes at display 210 and one or more inputs 212. The user interface device 208 is a virtual reality (VR) and/or augmented reality (AR) device or apparatus, for example, a wearable VR headset, that may be used to display a multidimensional rendering received from the image rendering module 206 and to allow an operator to interact with the multidimensional rendering. The user interface device 208 includes a display 210 to display multidimensional renderings. Display 210 of the user interface device 208 allows an operator to view a multidimensional rendering of multiple slices of MRI images received from the image rendering module 206. For example, the slices may show several common views of the heart as shown in the example slices of FIG. 3.

The user interface device 208 also includes one or more inputs configured to receive commands from the operator and to allow the operator to interact with a multidimensional rendering. User interface device 208 and input(s) 212 are configured to provide a variety of interactions that allow an operator to, for example, rotate the coordinate frame, resize the rendered image, dynamically adjust the window or level, etc. The actions (or options) available to an operator via user interface device 208 may also include ones pertaining to a pre-calibrated parallel imaging implementation as described above, such as view pre-calibrated slices, view slice numbers, select slices to image, toggle to show only imaged slices, and switch interaction modes, zoom, and rotate. The actions (or options) may be displayed as a menu on display 210 of the user interface device 208. For example, the menu may be implemented as a 3D menu that floats in system space and constantly orients itself to face the operator. In one embodiment, the visualization and interaction with the multidimensional rendering may be used during, for example, an interventional procedure. In another embodiment, features such as the resizing, rotation, and window/level adjustment may be used while retrospectively viewing datasets.

An operator may use the user interface device 208 to view all of the slices available for acquisition by the MRI system or view (e.g., by implementing a "tap" on the multidimensional rendering as discussed further below) number labels (e.g., individual slice numbers) to select a subset of the slices. Once a subset of slices is selected, the slice numbers for the selected subset of slices may be provided to the MRI system 202 (e.g., operator workstation 102 shown in FIG. 1) to image the subset of the total available slices. User interface device 208 may also show an operator which slices have ben pre-calibrated (e.g., for parallel imaging). In one embodiment, the user interface device 208 is a gesture capable device and interactions may be implemented through combinations of user gaze and hand gestures. In another embodiment, the user interface device a non-gesture capable device and interactions may be implemented using inputs such as buttons, switches, etc.

In an embodiment, the interactions available to an operator through user interface device 208 (e.g., via inputs 212) may include a "tap," "tap and drag," "double-tap," and "double-tap-and-drag." The tap and drag actions are meant to provide an intuitive and natural-feeling way to interact with a three-dimensional object. In a gestures-capable device, the start of a tap may be represented by the closing of the thumb and pointer (or index) finger together. The conclusion of a tap may be represented by the opening of the thumb and pointer finger. A double tap is two taps in rapid succession within a set period. In non-gesture-capable devices, a tap may be implemented via, for example, a click of a button. "Tap-and-drag" may be implemented via the three-dimensional change in absolute position of a multi-degree-of-freedom (multi-DoF) input device between the start and conclusion of a tap. In a gestures-capable device, this is the movement in user space of the hand that generated the tap. In a non-gestures-capable device, this is the movement in system space of the multi-DoF controller.

In an embodiment, user interface device 208 may provide two selectable modes. As mentioned above, the modes may be available to the operator via a menu on display 210, for example, a 3D menu that floats in system space and constantly orients itself to face the user. In this embodiment, the menu allows for the choice of either a "multi-slice" mode or a "rendering adjustment" mode. The render adjustment mode is configured to provide some of the features a physician would have in a standard radiology reading room, for example, resize and dynamic adjustment of the window and level. The operator is also able to rotate the multidimensional rendering (e.g., a hologram) to look at it from different views, rather than needing to walk around a fixed multidimensional rendering, which may be awkward and cumbersome in a crowded clinical area.

Rotations may be carried out by tap-and-drag gestures in the left/right and up/down directions. The delta in position of the input source is used to create a rotation of the rendering about the object's center of mass. In an embodiment where the user interface device is a wearable device, for example, a VR headset, the y-axis of the rotation coordinate system may be aligned to the current vertical orientation of the operator's head with rotation about the axis being controlled by the tap-and-drag in the left and right directions. The z-axis of the rotation coordinate system may be defined by the projection of the ray between the operator's head position and the rendering's center of mass of the system defined x-z plane. Rotation of the rendering about the rotation coordinate system may be controlled by tap-and-drag in the up and down directions. In an embodiment, rotation speed may be controlled by a mapping between a 1-meter unit cube centered around on the original position of the operator's input source at the time the tap is started and the rotation range from −180 degrees to 180 degrees (e.g., movement of the user's input source 0.5 meters to the left results in a −0.5 meter input, mapping to a rotation of −180 degrees about the rotation coordinate system's y-axis.).

An operator may adjust the rendering's scale using a tap-and-drag in the in/out (toward and away from the user) direction. Scaling speed is exponential, with movement within the unit cube mapping to a factor of two change in size in either direction (e.g., movement of the user's input source 0.5 meters towards the user results in an input of 0.5 meters, mapping to a change in scale of 2×). Control of the rendering's appearance may be controlled via a double-tap-and-drag, with level adjusted by movement in the left/right direction and window adjusted by movement in the up/down direction. The speed of the change in window and level is adjustable, and mapped to the unit cube as described above.

In the "multi-slice" mode, the operator toggles between viewing all of the available, pre-calibrated slices, and viewing just the slices that are currently being imaged in real-time. In an embodiment, a gaze-dot may be generated from a forward ray-projection from the operator's head position. When all of the available slices are presented, the operator can align the gaze dot with individual slices, then "tap" to view a number label. The number is then used to control which slices are scanned by selecting the corresponding numbers in, for example, an operator interface of the operator workstation 102 (shown in FIG. 1) of the MRI system 202. In another embodiment, real-time feedback may be provided between the multidimensional rendering (via user interface device 208) and the operator workstation of the MRI system, namely, the operator would be able to select which slices to image by interacting only with the rendering. For example, a "tap-and-hold" gesture input to the user interface device 208 would direct the MRI system 202 to start imaging at a different slice position. In another embodiment, "double taps" may be used to toggle between viewing all acquirable slices or only displaying the currently imaged slices.

Image reconstruction module 202, image rendering module 204 and user interface device 208 may be coupled to each other and communicate over wired or wireless connections. A communication protocol may be provided that specifies what information must be transmitted in each networking packet between the components of system 200 and the scheduling of packets. As discussed above, slice data may be acquired, reconstructed and transmitted to the image rendering module 206 on a sequential slice-by-slice basis. In one embodiment, the rendering may be updated only when all of the slices in a frame are available. Alternatively, the rendering may be updated each time a slice is reconstructed. Accordingly, the communication protocol is configured so that each slice is transmitted from the image reconstruction module 204 to the image rendering module 206 with its corresponding slice number and a Boolean flag indicating whether the slice is the last one in its frame. Optionally, a "bulk update" flag may be turned on to only update renderings when all co-acquired images are ready.

In an embodiment, scan settings may be provided in an initialization frame that includes a Boolean flag that is configured to select one of two separate communication protocols: 1) a communication protocol that is used for planar scans; and 2) a communication protocol that is used for volumetric scans. In this embodiment, data is transmitted unidirectionally from the image reconstruction module 204 to the image rendering module 206. Table 1 illustrates an exemplary format and content of the initialization frame.

TABLE 1

| Datatype | Unit16 × 3 | Float × 3 | Bool | Uint16 |
|---|---|---|---|---|
| Content | Matrix size | FOV Dimensions | Volumetric Switch | Data Buffer Size |

In the initialization frame, the third dimension of matrix size will be the total number of slices per frame for 2D datasets, or the number of partitions for 3D datasets.

Table 2 shows the format and content for a communication protocol used for a planar scan data transfer. In an embodiment, each of the data in the planar scan protocol are followed by a standard break character defined in code, for example, the float '9000'.

TABLE 2

| Datatype | Uint32 | Uint32 | Float × 3 | Float × 4 | Bool | Uint16 × (Matrix_x * Matrix_y) |
|---|---|---|---|---|---|---|
| Content | Frame Index | Slice Index | Slice Position (Vector3) | Slice Rotation (Quaternion) | Flag to refresh the rendering after receiving this slice | Slice Pixel Intensities (Order: Y locations for each X location. IE: Sequential Rows of Data) |

Table 3 shows the format and content for a communication protocol used for volumetric scan data transfer. In an embodiment, each of the data in the planar scan protocol are followed by a standard break character defined in code, for example, the float '9000'.

TABLE 3

| Datatype | Uint16 × (Matrix_x * Matrix_y * Number_Slices) |
|---|---|
| Content | Slice Pixel Intensities (Order: Y Locations for each X Location for each slice. IE: Sequential slices of sequential rows of data) |

Uint16 data transfer for pixel intensities assumes a grayscale value within the 16-bit unsigned integer range.

Figure 4:
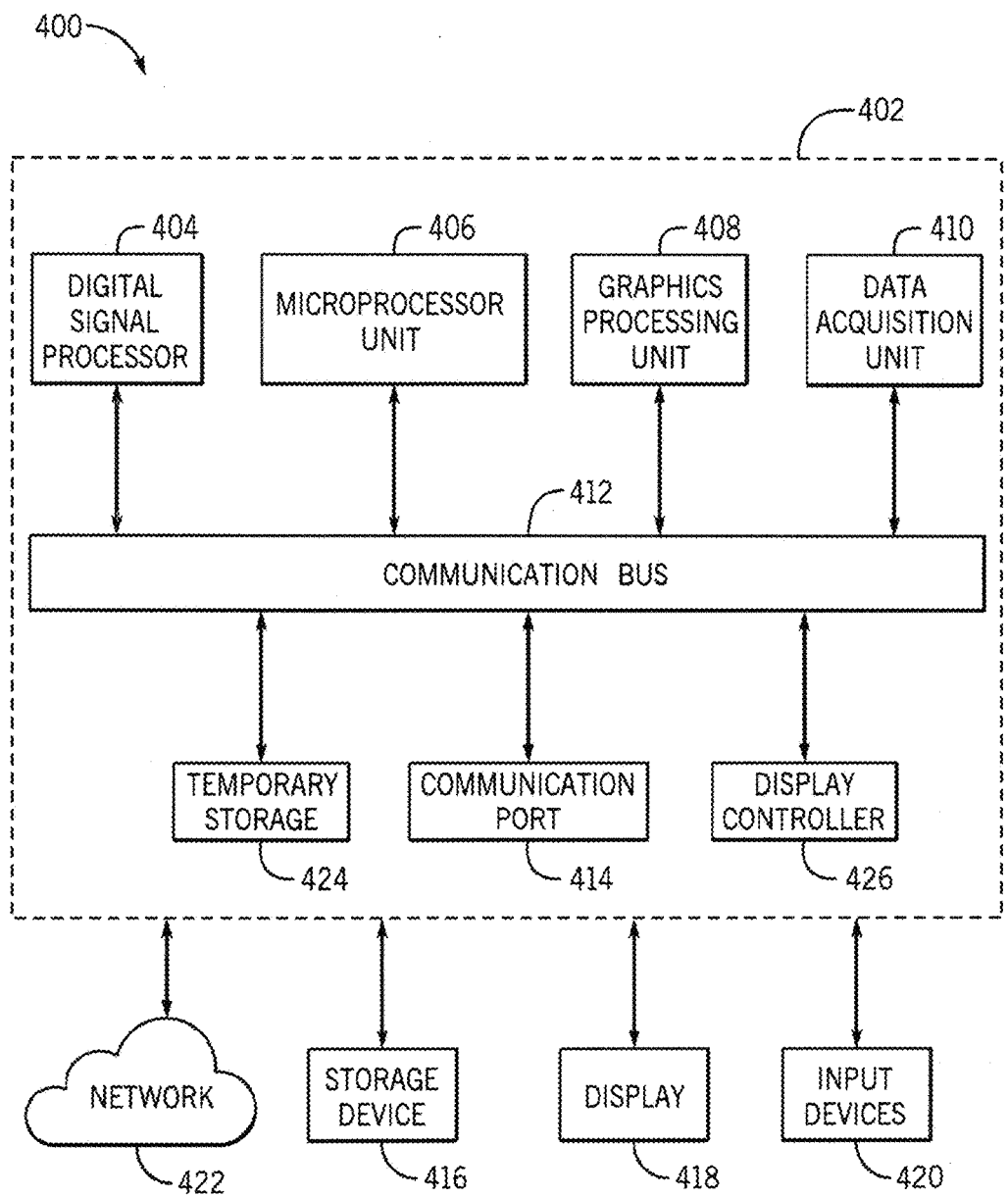
FIG. 4 is a block diagram of an example computer system in accordance with an embodiment.

FIG. 4 is a block diagram of an example computer system in accordance with an embodiment. Computer system 400 may be used to implement the methods described herein. In some embodiments, the computer system 400 may be a workstation, a notebook computer, a tablet device, a mobile device, a multimedia device, a network server, a mainframe, one or more controllers, one or more microcontrollers, or any other general-purpose or application-specific computing device. The computer system 400 may operate autonomously or semi-autonomously, or may read executable software instructions from the memory or storage device 416 or a computer-readable medium (e.g., a hard drive, a CD-ROM, flash memory), or may receive instructions via the input device 420 from a user, or any other source logically connected to a computer or device, such as another networked computer or server. Thus, in some embodiments, the computer system 400 can also include any suitable device for reading computer-readable storage media Data, such as data acquired with an MRI system (e.g., MRI system 100 shown in FIG. 1), may be provided to the computer system 400 from a data storage device 416, and these data are received in a processing unit 402. In some embodiment, the processing unit 402 includes one or more processors. For example, the processing unit 402 may include one or more of a digital signal processor (DSP) 404, a microprocessor unit (MPU) 406, and a graphics processing unit (GPU) 408. The processing unit 402 also includes a data acquisition unit 410 that is configured to electronically receive data to be processed. The DSP 404, MPU 406, GPU 408, and data acquisition unit 410 are all coupled to a communication bus 412. The communication bus 412 may be, for example, a group of wires, or a hardware used for switching data between the peripherals or between any component in the processing unit 402

The DSP 404 may be configured to implement the methods described here. The MPU 406 and GPU 408 may also be configured to implement the method described here in conjunction with the DSP 404. For example, the MPU 406 may be configured to control the operation of components in the processing unit 402 and can include instructions to implement the methods described in the present disclosure, including image reconstruction and image rendering, as described above, on the DSP 404.

The processing unit 402 may also include a communication port 414 in electronic communication with other devices, which may include a storage device 416, a display 418, and one or more input devices 420. Examples of an input device 420 include, but are not limited to, a keyboard, a mouse, and a touch screen through which a user can provide an input. The storage device 416 may be configured to store data, which may include data acquired with an MRI system, magnetic resonance images, calculated contrast concentration curves, estimated quantitative parameters, and/or quantitative parameters maps, whether these data are provided to, or processed by, the processing unit 402. The display 418 may be used to display images and other information, such as magnetic resonance images, patient health data, and so on.

The processing unit 402 can also be in electronic communication with a network 422 to transmit and receive data and other information. The communication port 414 can also be coupled to the processing unit 402 through a switched central resource, for example the communication bus 412. The processing unit can also include temporary storage 424 and a display controller 426. The temporary storage 424 is configured to store temporary information. For example, the temporary storage 424 can be a random access memory.

Computer-executable instructions for visualizing and interacting with MRI data in three and four dimensions in real-time according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly states, are possible and within the scope of the invention. The order and sequence of any process or method steps may be varied or re-sequenced according to alternative embodiments.

The invention claimed is:

1. A system for displaying and interacting with magnetic resonance imaging (MRI) data acquired using an MRI system, the system comprising:
    an image reconstruction module configured to receive the MRI data and to reconstruct a plurality of images using the MRI data;
    an image rendering module coupled to the image reconstruction module and configured to generate at least one multidimensional image based on the plurality of images; and
    a virtual reality or augmented reality device coupled to the image rendering module and located proximate to a workstation of the MRI system, the virtual reality or augmented reality device configured to display the at least one multidimensional image in real-time and to facilitate interaction by a user with the multidimensional image in a virtual reality or augmented reality environment;
    wherein the virtual reality or augmented reality device is further configured to receive an input to select a set of slices to be imaged by the MRI system and to provide the selected set of slices to the MRI system to direct the MRI system to scan the selected set of slices to acquire a set of MR data for the selected set of slices.

2. The system according to claim 1, wherein the plurality of images includes a plurality of slices.

3. The system according to claim 1, wherein the virtual reality or augmented reality device is a virtual reality or augmented reality headset.

4. The system according to claim 1, wherein the virtual reality or augmented reality device is configured to receive at least one input from the user via a hand gesture.

5. The system according to claim 1, wherein the virtual reality or augmented reality device in configured to allow a user to perform at least one of rotate the coordinate frame of the multidimensional image, resize the multidimensional image and dynamically adjust the window or level.

6. The system according to claim 1, wherein the multidimensional image is a hologram.

7. The system according to claim 1, wherein the multidimensional image is a three dimensional image.

8. The system according to claim 1, wherein the multidimensional image is a four dimensional image.

9. The system according to claim 1, wherein the multidimensional image is generated during an interventional procedure and used to assist with guidance of an interventional device during the interventional procedure.

10. The system according to claim 1, wherein the image reconstruction module reconstructs the plurality of images using a parallel imaging technique.

11. A method for displaying and interacting with magnetic resonance imaging (MRI) data acquired using an MRI system, the method comprising:
    receiving the MRI data from the MRI system;
    reconstructing a plurality of images using the MRI data with an image reconstruction module;
    generating at least one multidimensional image based on the plurality of images using a image rendering module;
    displaying the at least one multidimensional image in real-time on a virtual reality or augmented reality device located proximate to a workstation of the MRI system;
    interacting with the multidimensional image in a virtual reality or augmented reality environment using the virtual reality or augmented reality device;
    selecting a set of slices to be imaged by the MRI system using the virtual reality or augmented reality device; and
    providing the selected set of slices from the virtual reality or augmented reality device to the MRI system to direct the MRI system to scan the selected set of slices to acquire a set of MR data for the selected set of slices.

12. The method according to claim 11, wherein the plurality of images includes a plurality of slices.

13. The method according to claim 11, wherein the virtual reality or augmented reality device is a virtual reality or augmented reality headset.

14. The method according to claim 11, wherein the virtual reality or augmented reality device is configured to receive at least one input from a user via a hand gesture.

15. The method according to claim 11, wherein interacting with the multidimensional image includes performing at least one of rotate the coordinate frame of the multidimensional image, resize the multidimensional image and dynamically adjust the window or level.

16. The method according to claim 11, wherein the multidimensional image is a hologram.

17. The method according to claim 11, wherein the multidimensional image is a three dimensional image.

18. The method according to claim 11, wherein the multidimensional image is a four dimensional image.

19. The method according to claim 11, wherein the multidimensional image is generated during an interventional procedure and used to assist with guidance of an interventional device during the interventional procedure.

20. The method according to claim 11, wherein reconstructing the plurality of images includes reconstructing the plurality of images using a parallel imaging technique.

* * * * *